(12) United States Patent
Jafari et al.

(10) Patent No.: US 12,318,158 B2
(45) Date of Patent: Jun. 3, 2025

(54) MICROROBOTIC SYSTEMS AND METHODS FOR ENDOVASCULAR INTERVENTIONS

(71) Applicant: Board of Regents of the University of Texas System, Austin, TX (US)

(72) Inventors: Amir Jafari, San Antonio, TX (US); Miltiadis Alamaniotis, San Antonio, TX (US); Teja Guda, San Antonio, TX (US); Dimitrios Miserlis, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 365 days.

(21) Appl. No.: 17/799,048

(22) PCT Filed: Feb. 12, 2021

(86) PCT No.: PCT/US2021/018026
§ 371 (c)(1),
(2) Date: Aug. 11, 2022

(87) PCT Pub. No.: WO2021/163615
PCT Pub. Date: Aug. 19, 2021

(65) Prior Publication Data
US 2023/0060639 A1 Mar. 2, 2023

Related U.S. Application Data

(60) Provisional application No. 62/975,691, filed on Feb. 12, 2020, provisional application No. 62/975,683, filed on Feb. 12, 2020.

(51) Int. Cl.
*A61B 34/32* (2016.01)
*A61B 34/20* (2016.01)
*A61B 34/30* (2016.01)
(Continued)

(52) U.S. Cl.
CPC .............. *A61B 34/32* (2016.02); *G06N 5/048* (2013.01); *A61B 2034/2065* (2016.02);
(Continued)

(58) Field of Classification Search
CPC . A61B 34/32; A61B 34/20; A61B 2034/0265; A61B 2034/301;
(Continued)

(56) References Cited

U.S. PATENT DOCUMENTS

2014/0275982 A1* 9/2014 Hendrick ............... A61B 90/98
606/130
2018/0028268 A1 2/2018 Nowlin et al.
(Continued)

OTHER PUBLICATIONS

Qi et al., "Fuzzy logic control of a continuum manipulator for surgical applications," 2014 IEEE International Conference on Robotics and Biomimetics (ROBIO 2014), Bali, Indonesia, 2014, pp. 413-418, doi: 10.1109/ROBIO.2014.7090366. (Year: 2014).*
(Continued)

*Primary Examiner* — Tan-Uyen T Ho
*Assistant Examiner* — Cherie M Poland
(74) *Attorney, Agent, or Firm* — Thomas | Horstemeyer, LLP

(57) ABSTRACT

Embodiments of the present disclosure provide robotic systems, apparatuses, and methods. One such robotic system comprises a robotic surgical tool; and a steering system configured to steer the robotic surgical tool based on motion angle commands along X and Y axes as the robotic surgical tool moves in an Z axis direction within a tubular passageway. The system further comprises a computing device that executes an artificial intelligence program configured to control the steering system by computing the motion angle commands based on a current position of the robotic surgical tool along planar axes of the tubular passageway and center (Continued)

positions of the passageway along the planar axes. Other systems and methods are disclosed.

18 Claims, 16 Drawing Sheets

(51) Int. Cl.
 *A61M 25/01* (2006.01)
 *G06N 5/048* (2023.01)

(52) U.S. Cl.
 CPC ... *A61B 2034/301* (2016.02); *A61B 2034/303* (2016.02); *A61M 2025/0166* (2013.01)

(58) Field of Classification Search
 CPC .... A61B 2034/303; A61B 2017/00539; A61B 2017/00318; G06N 5/048; G06N 3/043; A61M 2025/0166; G05B 2219/40193
 See application file for complete search history.

(56) References Cited

U.S. PATENT DOCUMENTS

| | | | |
|---|---|---|---|
| 2018/0055577 A1 | 3/2018 | Barral et al. | |
| 2018/0279909 A1* | 10/2018 | Noonan | A61B 90/37 |
| 2018/0296281 A1* | 10/2018 | Yeung | A61B 34/32 |
| 2018/0344284 A1 | 12/2018 | Freudenberger et al. | |
| 2019/0209811 A1* | 7/2019 | Friend | A61B 1/015 |
| 2019/0213382 A1* | 7/2019 | Zhang | A61B 1/00149 |

OTHER PUBLICATIONS

International Search Report and Written Opinion for International Application No. PCT/US2021/018026 mailed May 27, 2021.

* cited by examiner

Fuzzy Rules in FUZZY NAVIGATION

If X is LEFT, then AngleX is Positive
If X is EXACT, then AngleX is Constant  — Group 1 for X axis
If X is RIGHT, then AngleX is Negative If Y is LEFT, then AngleY is Positive
If Y is EXACT, then AngleY is Constant  — Group 2 for Y axis
If Y is RIGHT, then AngleY is Negative

FIG. 7

MICROROBOTIC SYSTEMS AND METHODS FOR ENDOVASCULAR INTERVENTIONS

CROSS-REFERENCE TO RELATED APPLICATIONS

This application is the 35 U.S.C. § 371 national stage application of International Application No. PCT/US2021/018026, filed Feb. 12, 2021, which claims priority to U.S. provisional application entitled, "Microrobotic Systems and Methods for Endovascular Interventions," having Ser. No. 62/975,683, filed Feb. 12, 2020, which is entirely incorporated herein by reference, and U.S. provisional application entitled "Microrobotic Systems and Methods for Gastrointestinal and Respiratory Interventions," having Ser. No. 62/975,691, filed Feb. 12, 2020, which is entirely incorporated herein by reference.

TECHNICAL FIELD

The present disclosure is generally related to autonomous robotic navigation techniques, such as in surgical operations.

BACKGROUND

Despite the numerous advances in medical technologies, clinicians still have difficulty in addressing certain endovascular conditions, such as acute aortic pathologies and ischemic stroke, which leads to high morbidity and mortality. One significant impediment to treating such conditions are the inherent limitations of available medical devices. In addition, surgeons often must complete advanced training at specialized training centers in order to be able to use the current medical devices intended for such applications. Furthermore, the variety of devices and equipment exchanges that are typically required to perform an endovascular procedure increase the duration and cost of the procedures. In addition to those drawbacks, both the patients and the medical personnel are often exposed to high doses of radiation when using existing medical devices as those devices must be operated under fluoroscopic guidance.

In view of the above facts, it can be appreciated that is would be desirable to have alternative systems and methods for performing endovascular procedures.

SUMMARY

Embodiments of the present disclosure provide robotic systems, apparatuses, and methods. One such robotic system comprises a robotic surgical tool and a steering system configured to steer the robotic surgical tool based on motion angle commands along X and Y axes as the robotic surgical tool moves in an Z axis direction within a tubular passageway. The system further comprises a computing device that executes an artificial intelligence program configured to control the steering system by computing the motion angle commands based on a current position of the robotic surgical tool along X & Z planar axes and Y & Z planar axes of the tubular passageway and center positions of the passageway along the X & Z planar axes and the Y & Z planar axes.

The present disclosure can also be viewed as a robotic method. In this regard, one embodiment of such a method, among others, can be broadly summarized by acquiring, by a computing device, sensor data indicating a current position of the robotic surgical tool within a tubular passageway; determining, by the computing device, the current position of the robotic surgical tool along X & Z planar axes and Y & Z planar axes of the tubular passageway and center positions of the passageway along the X & Z planar axes and the Y & Z planar axes; computing, by the computing device, motion angle commands that will steer the robotic surgical tool at a constant speed forward through the passageway along a Z axes; and sending, by the computing device, the motion angle commands to a controller for the robotic surgical tool.

In one or more aspects for such apparatuses and/or methods, the robotic surgical tool comprises an elongated, flexible, steerable cannula that includes multiple expansion-flexion microrobotic (EFMR) cannulation units (CUs) that are configured to be selectively stiffened or softened using non-Newtonian fluid compression; the robotic surgical tool is configured to move via flexible microrobotic expansion; the robotic surgical tool is configured to stiffen such that a stiff device is inserted within a cavity of the robotic surgical tool; and/or wherein the stiff device comprises a surgical stent.

In one or more aspects for such apparatuses and/or methods, the artificial intelligence program of the computing device utilizes a fuzzy logic model to determine the motion angle commands; an imaging device acquires real-time images of the current position of the robotic surgical tool within the tubular passageway and provides the real-time images to the computing device; and/or the real-time images comprise computed tomography angiograph (CTA) or intravascular ultrasound (IVUS) images.

In one or more aspects for such apparatuses and/or methods, the fuzzy logic model is configured to process the real-time images to produce fuzzy input parameters corresponding to the current position of the robotic surgical tool; process the fuzzy input parameters to produce fuzzy output parameters corresponding to motion angles for a next move of the robotic surgical tool; and process the fuzzy output parameters to derive motion angle values at which the robotic surgical tool is to be steered.

In one or more aspects for such apparatuses and/or methods, the tubular passageway comprises an aortic lumen or a bowel lumen; and/or the robotic surgical tool comprises an endograft instrument.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 7 shows exemplary Fuzzy rules of an exemplary navigation system in accordance with various embodiments of the present disclosure.

DETAILED DESCRIPTION

As described above, it would be desirable to have alternative systems and methods for performing endovascular procedures that avoid drawbacks of existing systems and methods. Disclosed herein are examples of such alternative systems and methods. In the following disclosure, various specific embodiments are described. It is to be understood that those embodiments are example implementations of the disclosed inventions and that alternative embodiments are possible. Such alternative embodiments include hybrid embodiments that include features from different disclosed embodiments. All such embodiments are intended to fall within the scope of this disclosure.

Disclosed herein are microrobotic systems based on advanced mechatronic technology for use in endovascular procedures. The microrobotic systems improve the speed, accuracy, safety, and reliability with which such procedures are performed and are suitable for integration into the standard of care for patients. The systems provide advanced three-dimensional microrobotic navigation with artificial intelligence support and real-time endoluminal imaging to decrease the need for fluoroscopy. In addition, the microrobotic systems are MRI-compatible. This is a major advantage over current medical devices used in endovascular procedures, which do not have such capability.

Figure 1A:
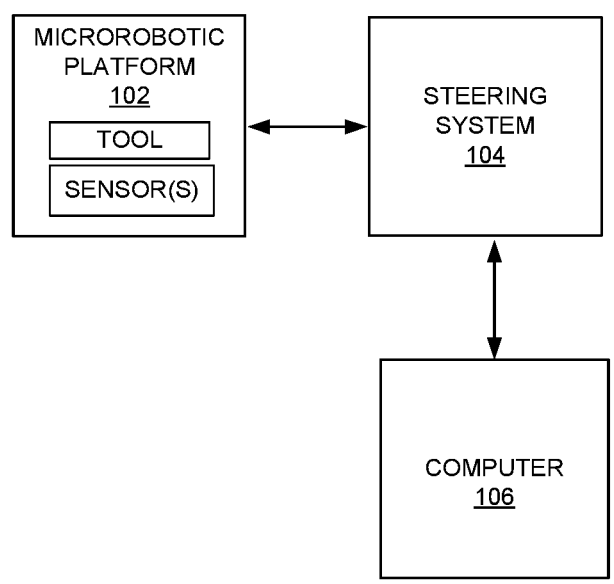
FIG. 1A is a block diagram of an exemplary microrobotic system in accordance with various embodiments of the present disclosure.

FIG. 1A shows a block diagram of an exemplary microrobotic system in accordance with various embodiments of the present disclosure. The microrobotic system 102 includes a microrobotic platform featuring a robotic tool, such as a robotic surgical tool, and one or more sensors or sensing devices, that can include imaging devices, such as an endoscopic camera, other imaging devices, or other sensors, that provide feedback data from application of the robotic tool. Accordingly, a steering system 104 can provide commands or controls to the microrobotic platform to guide operation of the robotic tool. Such commands can be based on inputs provided from sensing data from the one or more sensors of the microrobotic platform. The steering system 104 may utilize electrical and/or mechanical controls, including hydraulic controls—differential pressure and/or expansion—to steer the direction of the propagation, in various embodiments. The computation or determination of the platform commands can be provided by a computer 106 (computing device) that implements artificial intelligence models, such as fuzzy logic techniques, in accordance with various embodiments of the present disclosure. Such models can be employed in the computer 106 and/or controller as part of the control process for the microrobotic platform and be used to build a suitable rule-base and inference mechanism for calculating motion angles for autonomously steering a microrobotic tool via motion angle commands relayed by the steering system 104.

In some embodiments, a robotic tool 102 of microrobotic systems is specifically configured for use in aortic procedures. In such cases, the microrobotic systems enable accurate endograft placement without the need for multiple ancillary devices, such as wires, catheters, sheaths, and the like. In addition, the systems enable the ability for repositioning of an endograft in situations of graft migration and acute malperfusion (acute occlusion of critical branches of the aorta). The systems further facilitate control of complications, such as aortic rupture and aortic branch reperfusion, in the care of patients with acute aortic trauma. Additionally, the systems protect vessel walls from stress in order to prevent vessel wall injuries during the intervention. The systems support in situ mechanical retrieval of endovascular "trash" (e.g., a stent lost in a vessel) and in situ graft fenestration technology that enables the placement of openings on the endograft so as to enable redirection of the blood supply.

In other embodiments, the microrobotic systems are specifically configured for accessing the various aortic branches so that control can be exercised over them. The branches can be isolated from aortic circulation and connected to an extracorporeal circuit, such as the broadly utilized extracorporeal membrane oxygenation (ECMO) system. This endovascular debranching technique is not feasible with the currently available medical devices. Furthermore, the microrobotic systems enable emergent reperfusion for traumas, aneurysm ruptures, and more.

In still other embodiments, the microrobotic systems are specifically configured for use in cerebral arteries. In such cases, the systems can be used to perform ischemic stroke thrombectomies (i.e., removal of an arterial obstruction). One advantage of the systems in this context is rapid deployment of a suction sheath with microrobotic navigation and decreased need for ancillary equipment, radiation, and advanced neurointerventional training, to decrease ischemia time and complications.

In one embodiment, a microrobotic system in accordance with this disclosure comprises an elongated, flexible, steerable cannula that includes multiple expansion-flexion microrobotic (EFMR) cannulation units (CUs), i.e., tubular vascular cannulas, that are guided by artificial intelligence. The cannula can be navigated through vessel lumens, including branches of arteries, to perform a given intervention, such as removal of a thrombus. Differential non-Newtonian fluid (NNF) compression (or an equivalent mechanism) is used to adjust the stiffness/rigidity of the cannula as needed. The system also includes a steering mechanism that is controlled by an autonomous system that utilizes artificial intelligence to enable smooth coordination, stability, accuracy, and reliability of control over the cannula. Notably, unlike current systems in the market, the microrobotic system does not rely upon wires or microactuators for steering.

In various embodiments, microtubes (which will be used as air-pressure channels for steering) are used to create coaxial channels in a tubular configuration to create the body of the flexible microrobot. Additionally, non-Newtonian Fluid (NNF) channels (for adjusting the flexible microbotic device stiffness) are injected inside the steering microtubes. In various embodiments, the microtubes may be formed from low-density polyethylene sheets and/or polydimethylsiloxane (PDMS) materials. A variety of materials can be used as the NNF in certain embodiments, including a mixture of highly branched polysaccharide polymer, synthetic material which comply to FDA (Food and Drug Administration) rules, etc.

Accordingly, expansion of the flexible body of the microrobot will be based on longitudinally-growing channels embedded coaxially and steering the device will be based on asymmetric expansion (only some channels selectively expanded). By fine incremental control of channel growth, fine steering can be achieved without the use of wires. While the EFMR is moving from the initial point to the target point, it maintains maximum flexibility to prevent damage to the fluidic passageway, e.g., vascular wall tissue, and at the same time, maintains its optimal steering capability. Once a target point has been reached, the "shaft-body" of the microrobot tool can be stiffened in order to provide a "safe" enlaced pathway or cavity that can be used to insert various other devices, such as, but not limited to, stents. The aforementioned stiffening will not change microrobot morphology by embedding another set of longitudinal channels filled with a novel non-Newtonian fluid (NNF) inside the EFMR body. Pertinent properties of the NNF is the viscosity which can be dramatically increased by small change in the pressure of each channel. Increased viscosity of the fluid trapped inside each channel will lead to increased stiffness of the FMR body by increasing the pressure inside the NNF filled channels.

Figure 1B:
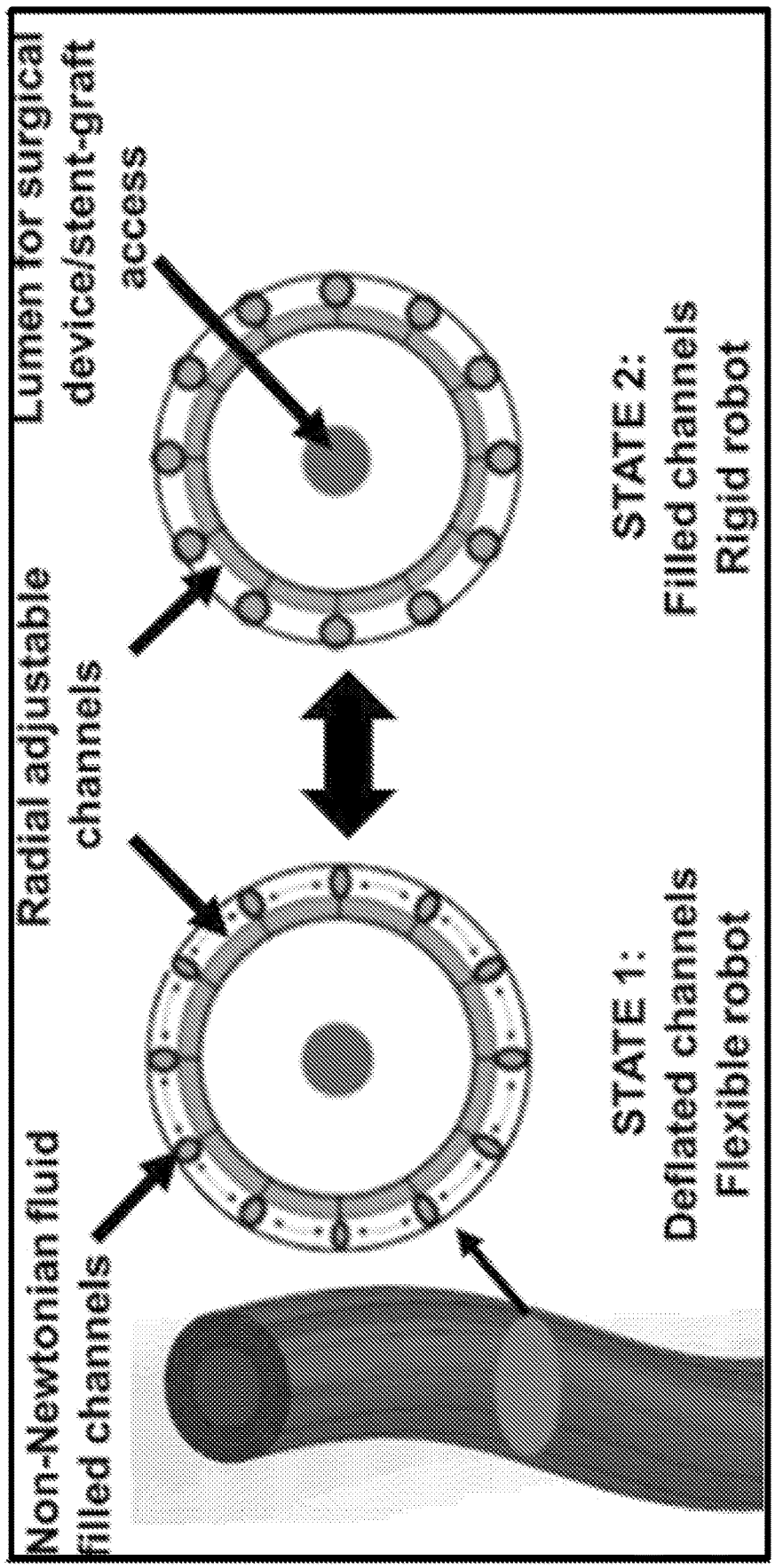
FIG. 1B shows an exemplary structural unit for steerable cannulas with adjustable stiffness in accordance with various embodiments of the present disclosure.

FIG. 1B shows a schematic of an exemplary embodiment of a flexible microrobotic device body ("microbot") (left) and cross-sections (middle and right) that depict adaptive microtubes/channel configuration symmetrically around a central axis in accordance with various embodiments of the present disclosure. The whole body of the exemplary microrobot will be stiffened without changing its shape (configuration). Having a stiff hollow path, protects the target from injuries while inserting stiff devices (e.g., stents) inside the human body. The exemplary flexible microrobotic device (FMR), is designed to maintain its stability with zero deflection (because of its inherent adaptive material stiffness), independent of the distance the device is inserted into the target structure.

The microrobotic system includes the following aspects/features. First, functional (device-specific) compartments and working compartments for third-party surgical device integration (adjustable to each device's needs). Second, expansion with the use of combined expansion of functional cannulas and continuous compartment intussusception of the working sheath. This creates a controlled forward expansion, limiting the shearing friction on the outer wall layer and providing accurate multidirectional navigation ability, with tapered diameter adjusted to certain devices or flexible expansion in others. This flexible microbotic expansion is an advancement over current telescoping, accordion, or singular eversion growth systems.

Third, adjustability of not only the rigidity based on the navigation pressure control cannulas (hydraulic and other mechanisms) but also the outer procedural device rigidity to continuously protect the tissues from damage based on their quality, third-party surgical device integration needs, procedural steps, and the specific intervention target. The real-time rigidity adjustment is based on NNF compression and other material properties, as well integrated mechanisms adjusted for each device. The differential analog control (pressure, etc.) is supported by the artificial intelligence control system. Fourth, device navigation, rigidity, and intervention functions are controlled in an analog fashion, which provides an advantage for fine control of the system, continuous feedback from the real-time procedural needs and continuous sensor data or feedback, uniformity in steering, and the ability to conform to any geometrical feature.

Fifth, the system control implements artificial intelligence for operator support, function refinement, and control. Sixth, the material design technology supports the high-pressure support needs of each individual device to create a stable system for operation and accommodation of third-party medical devices for implantation and intervention. Lastly, the system is able to integrate sensors, including ultrasound guidance and other sensors (including third-party devices), for navigation and diagnostic or intervention purposes.

In various embodiments, the three-dimensional EFMR is a soft microrobot based on flexible material. It is a compartmentalized but continuous microrobot made out of soft material to navigate through various environments using expansion as a method for navigation. Unlike the traditional robots that move by surface contact via "pushing" on the surface, this new technology relies on expansion to move forward. The microrobot utilizes a forward flexible motion based on expansion of cannulas and intussusception (folding back on itself). As such, it "lays and walks." The microrobot has a stationary portion and can expand by folding material. Therefore, the body lengthens as the material extends at the tip but the rest of the body does not move and thus there is no relative movement between the microrobot's body and the environmental surface. So, the microrobot can lengthen without any friction caused by relative movement. In other words, the device is capable of expanding with the use of a combined expansion of functional cannulas (tubes with pressure inside growing) and continuous compartment intussusception of the working sheath, which creates a controlled forward expansion, limiting the shearing friction on the outer wall layer.

Figure 1C:
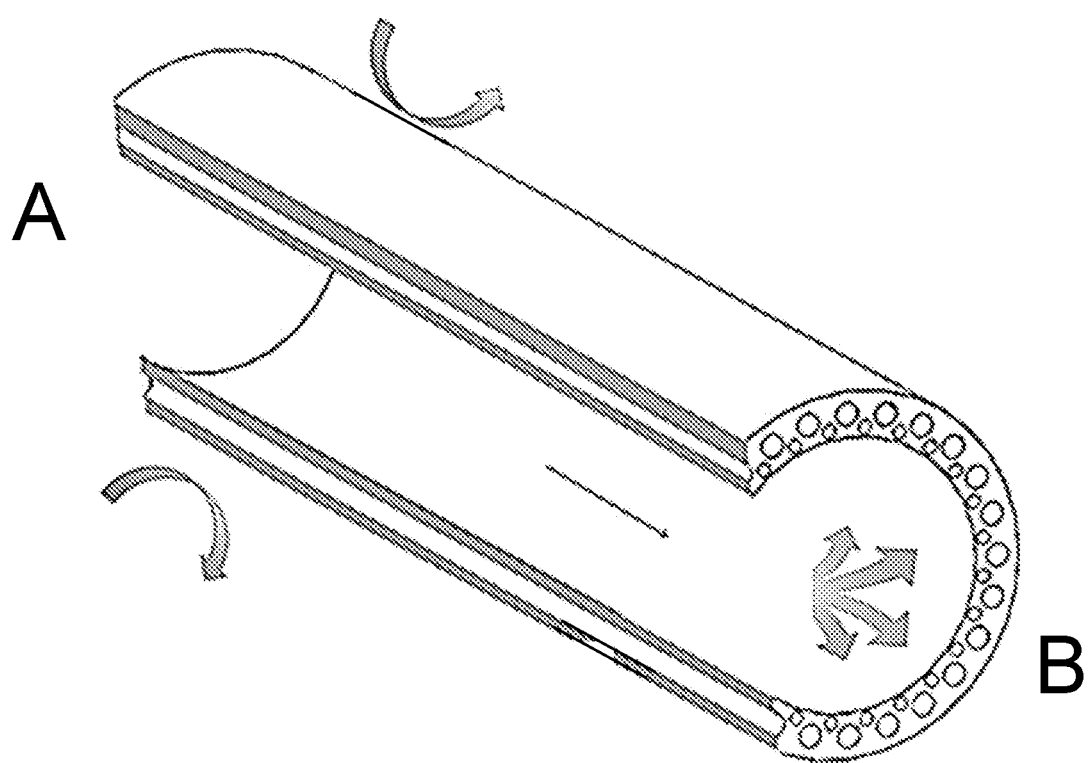
FIG. 1C is a perspective view of an embodiment of a flexible and expandable microrobot of a microrobotic system.

The microrobot tool's softness and its capability to expand across distances without moving the whole body make it an excellent candidate for medical applications requiring safe human and microrobot interaction. For instance, instead of a conventional tube that is pushed through the lumen, the EFMR can navigate without dragging along or injuring delicate and vulnerable structures and tissues (e.g., arterial dissection in a diseased artery). The microrobot works on the principle of flexible expansion and intussusception, a next-generation system more advanced than current flexible microrobotic systems. The expansion is possible because of the hydraulic pressure against the microrobot's body, which comprises a multi-compartmented but continuous system made of soft material that expands and folds within itself. This enables navigation of the microrobotic tool in multiple directions as the functional compartments expand and fold with differential pressure. This is illustrated in FIG. 1C. By creating differential pressure, the system can steer and navigate the microrobotic tool in an analog fashion. This provides three-dimensional device control along the path traversed by the EFMR.

Figure 2:
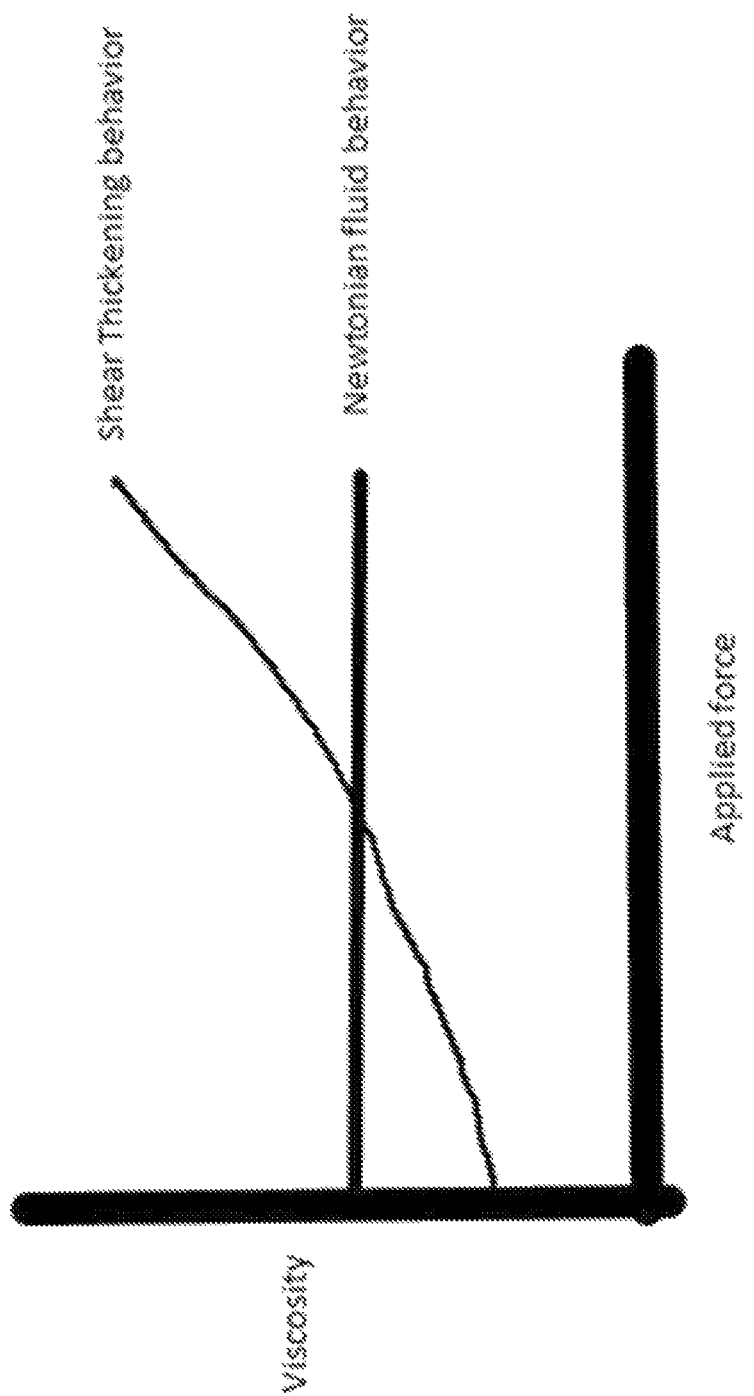
FIG. 2 is a graph that shows the behavior of non-Newtonian fluids in response to shear.

Another significant aspect of the microrobotic system is the ability to adjust the stiffness/rigidity of the microrobotic tool once the target is reached. Many biomedical applications require endoluminal navigation through a complex three-dimensional pathway and, at the same time, create a strong support system (like a railway rail). This helps to create a stable system for an intervention without putting a lot of stress on the walls of the biological structure, which can injure the surrounding biologic tissues (e.g., rupturing a calcified artery with a stiff wire-sheath system). In some embodiments, the stiffness is adjusted using selective pressure activation of a non-Newtonian fluid (NNF) in the microrobotic device body (or equivalent soft material system) once it has conformed in shape after it has reached its target. The result is a stable support system shaft available for further interventions without increasing the stress on the walls of the surrounding structures (i.e., bending biological structure like tortuous calcified arteries). The nature of the fluid results from the interactions between particles in suspension, known as discontinuous shear thickening (DST). The viscosity of the fluid varies with shear rate and, by applying shearing force, the fluid becomes more viscous. At a critical shear rate, the viscosity of a DST fluid spikes and solid-like behavior results, as illustrated in FIG. 2.

After the stabilization of the cannulation path by solidifying the soft microrobot's body, additional devices already used in endovascular procedures, such as wires and catheters, can be used as well, depending on the intervention and proceduralist preferences. As such, the microrobotic system has broad compatibility with FDA-approved medical devices.

Movement of the microrobotic tool can include the ability to move in all directions—360 degrees, forward and backwards, and advance towards a target from (point A to B in FIG. 1C), maintain control of the location of the robotic shaft during the navigation in this tubular structure, with various diameter changes, various turning points and branching points. Exemplary operations for which the microrobotic tool can be applied, include, but are not limited to, endovascular navigation, an aortic lumen with branching points, colonoscopy in the large bowel or endoscopy in the stomach and small bowel, bronchoscopy in the tracheobronchial tree, or any general operation requiring movement from within small controlling tubes arranged circumferentially.

In various embodiments, the microrobotic tool is controlled by a software-based navigation system that utilizes artificial intelligence. In particular, the navigation system is implemented using intelligent tools such as fuzzy logic, neural networks, and combinations thereof. The artificial intelligence navigation system acquires information from the microrobot sensors (e.g., imaging) and makes decisions regarding the next move of the microrobot. The advantage offered by the use of artificial intelligence is that the microrobot can move autonomously (or semi-autonomously with input for the surgeon-operator) within the body of the patient without damaging any tissues. The use of fuzzy logic greatly benefits the representation of the acquired knowledge from the sensors, while neural networks provide the distance and the direction that the movement should comprise. Except for the aforementioned tools, other tools from the artificial intelligence library can also be used to implement the artificial intelligence brain of the microrobot. The goal is to have better navigation ability with artificial intelligence coordination of the microrobotic system, accurate target control, operator support to assist complex operative maneuvers, increased safety of the operation, and decreased the operative time.

In the last decade, artificial intelligence (AI) has found wide use in several engineering and science domains. AI has found practical use by automating processes and/or analyzing data and making inferences. Endovascular operations are high risk surgeries that demand highly sensitive actions from the human operator. Robotics is one of the technologies that has been identified as being a key to increase the efficiency of the operations and will transform the way surgeons operate. Autonomous behavior can be attained by equipping the robot with a software module that implements algorithms from artificial intelligence. Notably, the use of artificial intelligence and intelligent systems in developing navigation systems in endovascular aorta operations is at a premature level. Thus, AI can play a significant role in vascular surgery operations. In particular, fuzzy logic is one of the well-known and widest tools found in AI realm with plenty of applications in various medical domains. The strength of fuzzy logic lies in its ability express knowledge as a set of overlapping sets while lumping together several numerical values by expressing them using a single linguistic term.

In accordance with embodiments of the present disclosure, a robotic tool has been developed for navigating tubular passageways implementing fuzzy logic methods and thus is capable of supporting robotic tools for endovascular operations. In various embodiments, such a fuzzy logic tool is equipped to navigate a surgical robot within the vascular systems of a patient with little intervention from the human operator, thereby allowing a robot to navigate in an autonomous way in the body of the patient, which minimizes the workload and intervention of the surgeon and reducing the time length of the surgery.

The present disclosure introduces a new methodology that utilizes fuzzy logic in robotic navigation controls that can be, but is not limited to being, deployed in cardiovascular operations which provides a new application of AI in the medical domain. In accordance with embodiments of the present disclosure, an exemplary novel navigation system is provided that implements a fuzzy inference system in order to make a robot act autonomously within the unknown and dynamically varying environment of an aorta.

Figure 3:
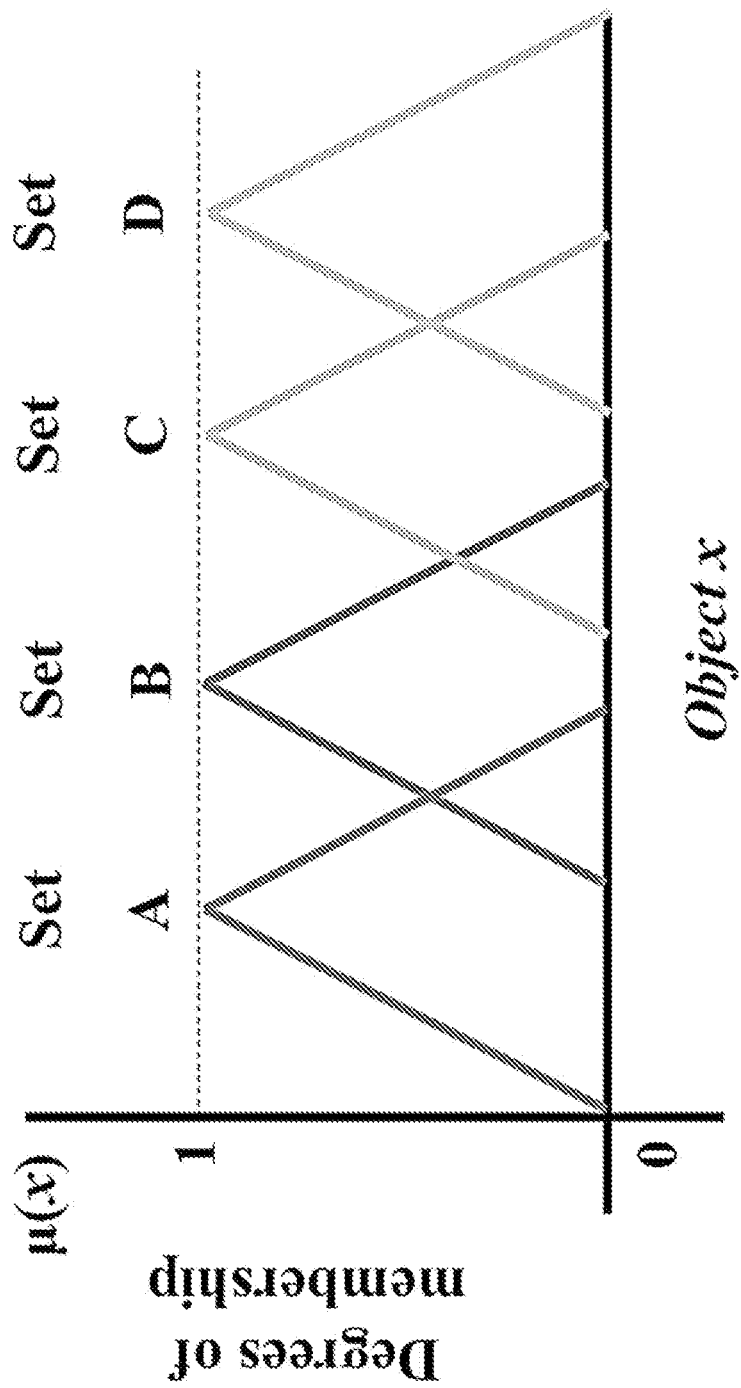
FIG. 3 shows an example of 4 fuzzy sets having triangular membership functions.

A main pillar of fuzzy logic is the use of fuzzy sets. A fuzzy set extends the definition of traditional sets. The theory of sets states whether an object belongs to a set or not—the logic is "digital"—while a fuzzy set may contain an object with a up to a degree. The degree with which an object belongs to a fuzzy set is called "degrees of membership" and is being determined by the membership function (usually denoted as $\mu(x)$). It should be noted that a fuzzy set has its own membership function that defines the set. The membership function assigns to an object a value in the range $[0, 1]$, where 0 denotes the full absence from the set, and 1 the absolute certainty that the object belongs to the set. Any values between 0 and 1 denote partial membership to the set. One of the strengths of fuzzy sets is that their membership function may overall allow one object to belong to more than one set. FIG. 3 provides an example of a group of 4 fuzzy sets that have triangular membership functions, while there is overlap among sets. It is this overall that models the inherent uncertainty in the problem data. Modeling via fuzzy sets allows the development of the associations among the fuzzy sets by utilizing IF/THEN rules. Therefore, fuzzy rules can be developed that take the following form:

IF $x$ is Set $A$, THEN $y$ is Set $W$ where x and y are variables that are modeled with different set of fuzzy sets. A group of fuzzy rules define a fuzzy algorithm and may be used to describe associations among various variables.

The output of a fuzzy algorithm is a fuzzy set. However, in real world applications the processing of a fuzzy set has no practical use. Therefore, there is a need to convert the fuzzy set to a single number—a process that is called defuzzification. There are several methods that have been proposed for defuzzification with the most used one being the "mean of area" defuzzification. Overall, the use of fuzzy sets, fuzzy rules and defuzzification consists of a fuzzy inference system (FIS). FIS have found wide use in several real-world applications.

In various embodiments, a goal of an exemplary navigation system is to provide autonomous navigation within a vascular aorta. Such a system is configured to allow the autonomous movement of a microrobot within the endovascular aorta. To that end, an exemplary navigation system utilizes information about a current position of the microrobot and make decisions on its next movement within the aorta. In various embodiments, an exemplary navigation system is implemented by means of fuzzy logic. For example, an embodiment of an exemplary navigation system for a microrobot can implement a FIS whose input is a current position of the microrobot and whose output is a position in the next time slot for the microrobot. The block diagram of an exemplary fuzzy logic navigation system is provided in FIG. 4, where certain individual steps are given. As such, the operation of an exemplary fuzzy logic navigation system is based on the following assumptions: the information on the current position of the microrobot is available via real-time medical imaging techniques; the information of the center of the aorta is known via real-time medical imaging techniques; and the microrobot moves forward with a constant speed. For purposes of the present disclosure, the movement is assumed to take place in the Z axis, as shown in FIG. 4.

Figure 4:
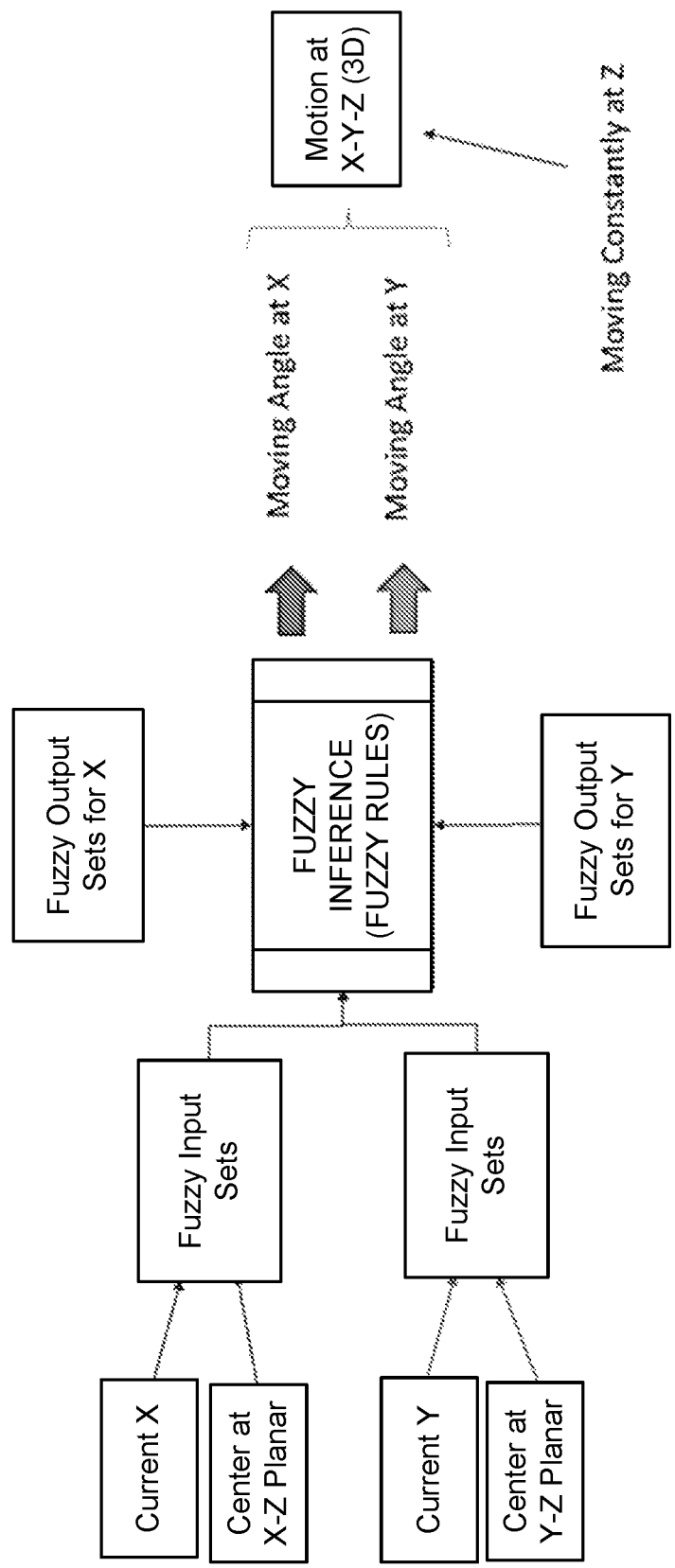
FIG. 4 is a block diagram of an exemplary fuzzy logic navigation system for endovascular operations in accordance with various embodiments of the present disclosure.
Figure 5:
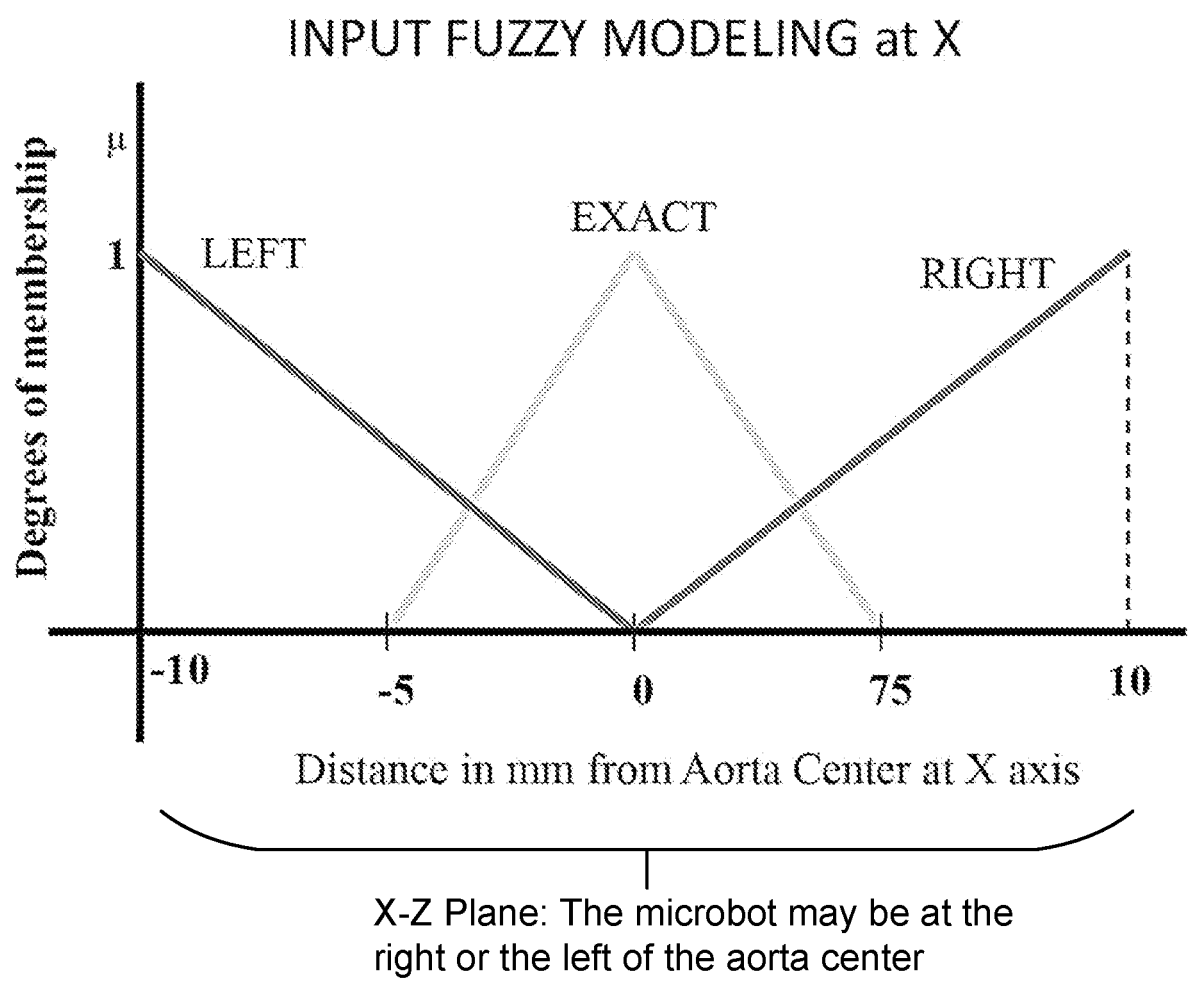
FIG. 5 shows an example of input fuzzy sets for the X-Z plane in accordance with various embodiments of the present disclosure.
Figure 6:
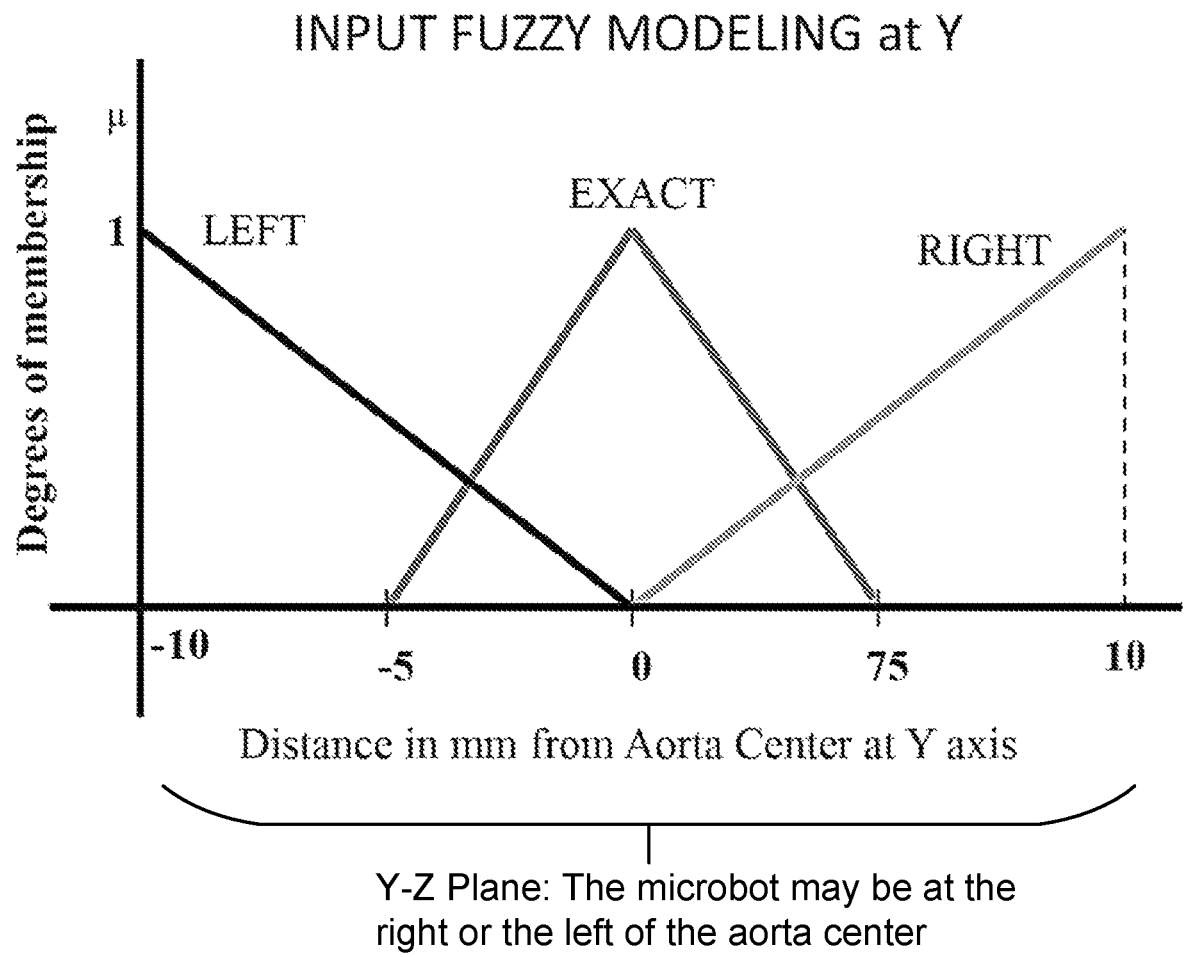
FIG. 6 shows an example of input fuzzy sets for the Y-Z plane in accordance with various embodiments of the present disclosure.

In FIG. 4, it is observed that the fuzzy navigation system receives four inputs: the current position in the axes X and Y, and the respective center positions at planar X-Z and Y-Z directions, respectively. In accordance with various embodiments, the input information can be obtained from imaging devices or cameras used during the endovascular operation. The input information is utilized to evaluate two variables as fuzzy input sets: (1) Distance at X axis: Current X—Center at X-Z plane; and (2) Distance at Y axis: Current Y—Center at Y-Z plane. Once the above values are found, then they are forwarded to the Fuzzy Inference System (FIS), where they get fuzzified via fuzzy sets. The fuzzy input sets that model the Distance at X variable are presented in FIG. 5 for the X-Z plane, while the fuzzy input sets that span the range of Distance at Y variable are presented in FIG. 6 for the Y-Z plane. In both figures, it is observed that the distances are modeled via the use of three fuzzy sets that span the range [-10, 10] mm for both variables, in an exemplary implementation. This range expresses the diameter of the aorta, where the value 0 denotes the center of the aorta, and the extreme values -10 and 10 express the left and the right boundary of the aorta in the axis respectively. It should be noted that the variables in FIGS. 5 and 6 are modeled with 3 fuzzy sets named as LEFT, EXACT, and RIGHT that express the location of the microrobot with respect to axis center.

Once the variables are fuzzified via fuzzy input sets, then they are forwarded to a next module of the FIS that includes a set of fuzzy rules, in accordance with various embodiments, in which exemplary fuzzy rules take the distance values and infer the angles at which the microrobot should move on each axis. It should be mentioned that given there are two angles to be determined—a first angle at the x axis and a second angle at the y axis, and therefore, there are two groups of rules. The rules employed in an exemplary fuzzy navigation system are provided in FIG. 7.

In FIG. 7, the fuzzy rules or inference associate the input variables that are in the left hand side of the rules in the form of a condition with the output variables that are in the right hand side of the rules. The fuzzy output variables are AngleX that denotes the angle at which the microrobot should move on the X axis and AngleY that expresses the angle at which the microrobot should move on the Y axis. The fuzzy rules or inference stage converts the output variables to a single moving angle for each of the X and Y axes as part of the defuzzification process.

Hence, the fuzzy navigation system determines the angles at which the robot should move in the axes X and Y, while the movement on Z axis is constant. Thus, the movement of the microrobot (in direction of moving angle at X and a moving angle at Y) is the synthesis of the movement in all three axes based on the values provided by an exemplary fuzzy navigation system.

Figure 8:
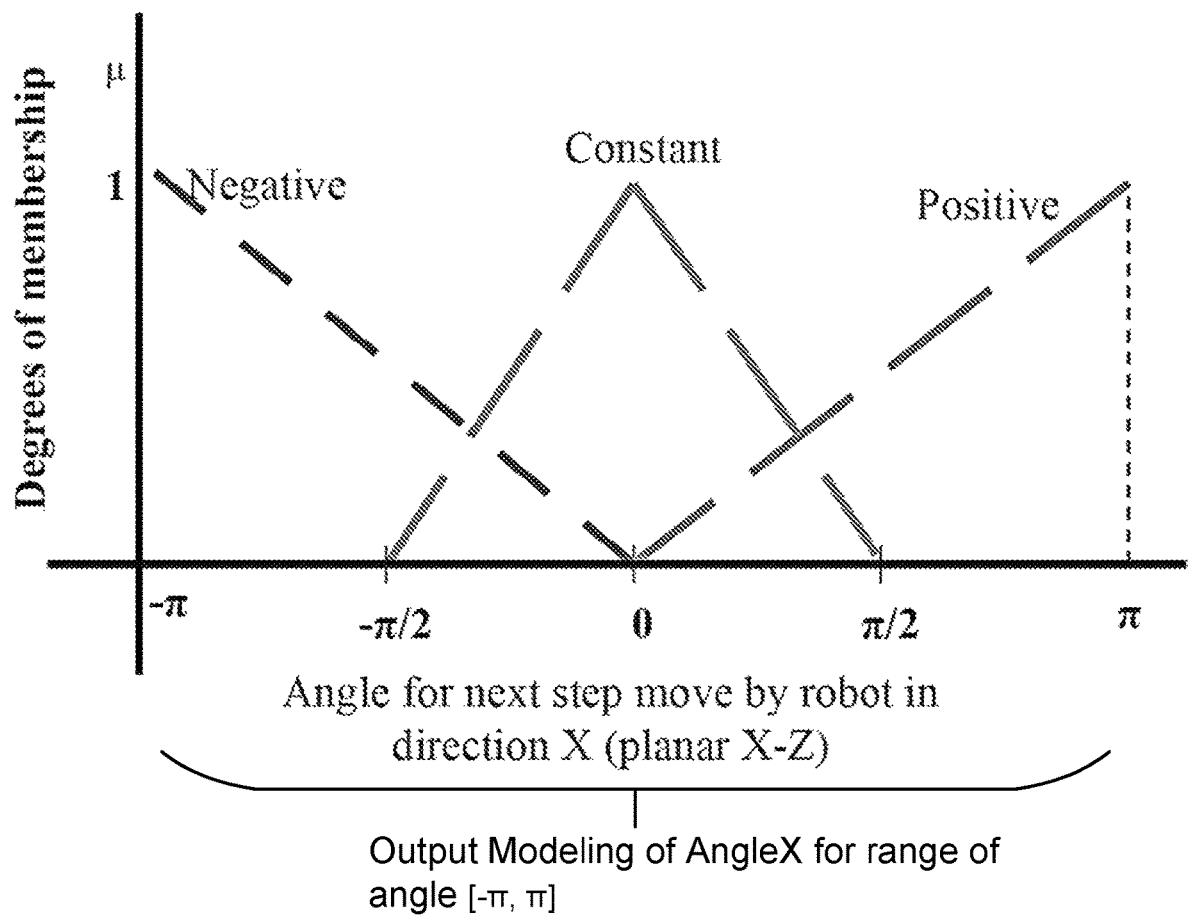
FIG. 8 shows exemplary Fuzzy output sets for modeling an output variable at which a microrobot tool should move on the X axis in accordance with various embodiments of the present disclosure.
Figure 9:
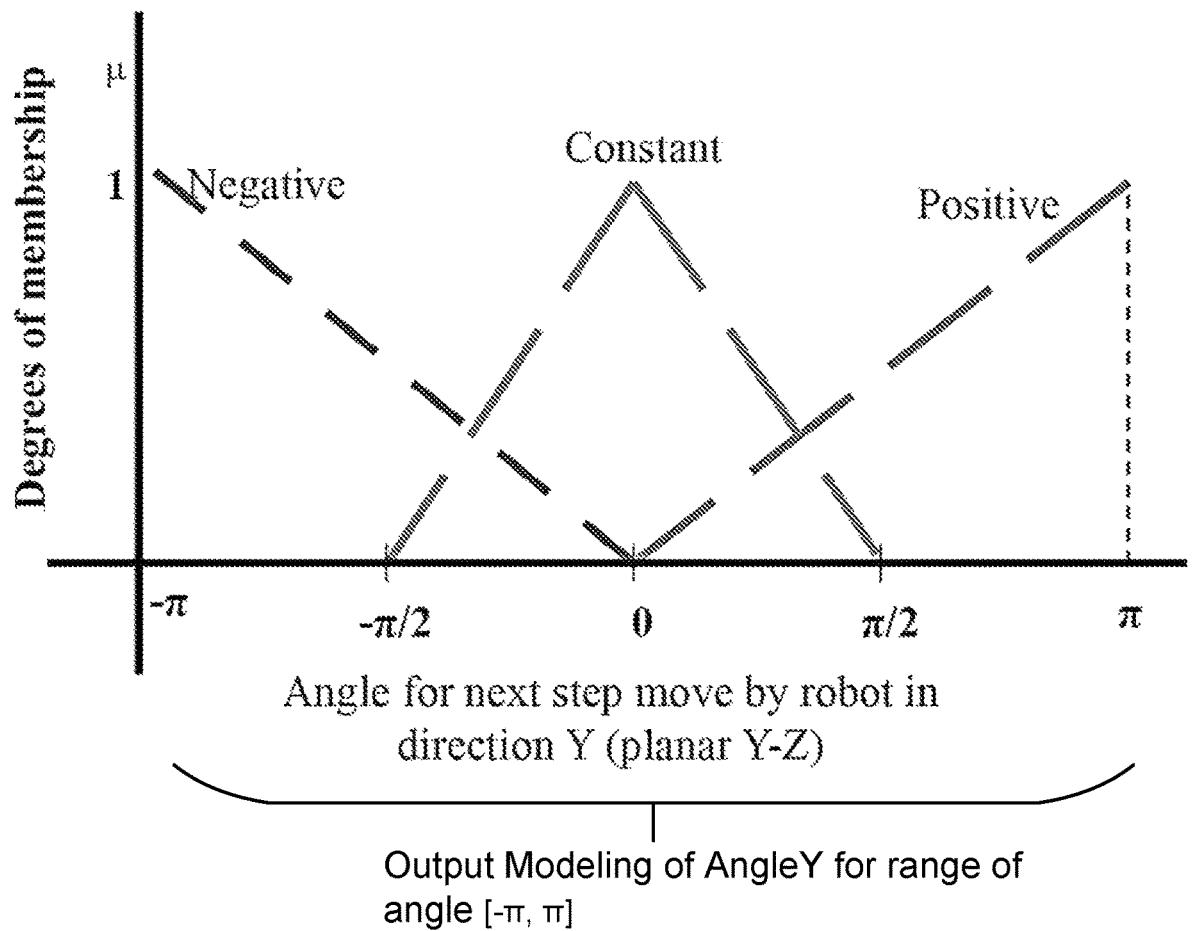
FIG. 9 shows exemplary Fuzzy output sets for modeling an output variable at which a microrobot tool should move on the Y axis in accordance with various embodiments of the present disclosure.

At this point, it should be noted that the variables AngleX and AngleY can be modeled via fuzzy output sets, as shown in FIG. 8 and FIG. 9, respectively. It is observed that the fuzzy outputs are spanned with 3 fuzzy sets, named as Negative, Constant, and Positive, which span the range [-π, π]. Lastly, the values can be defuzzified via a mean of area method. Accordingly, in accordance with embodiments of the present disclosure, one or more calculated steering parameters or motion angle commands may be obtained using a fuzzy logic model by processing input parameters corresponding to a current location of a microrobotic tool to produce fuzzy input parameters; processing the fuzzy input parameters to produce fuzzy output parameters; and processing the fuzzy output parameters to derive motion angles at which the microrobotic should drive or steer towards.

Figure 10:
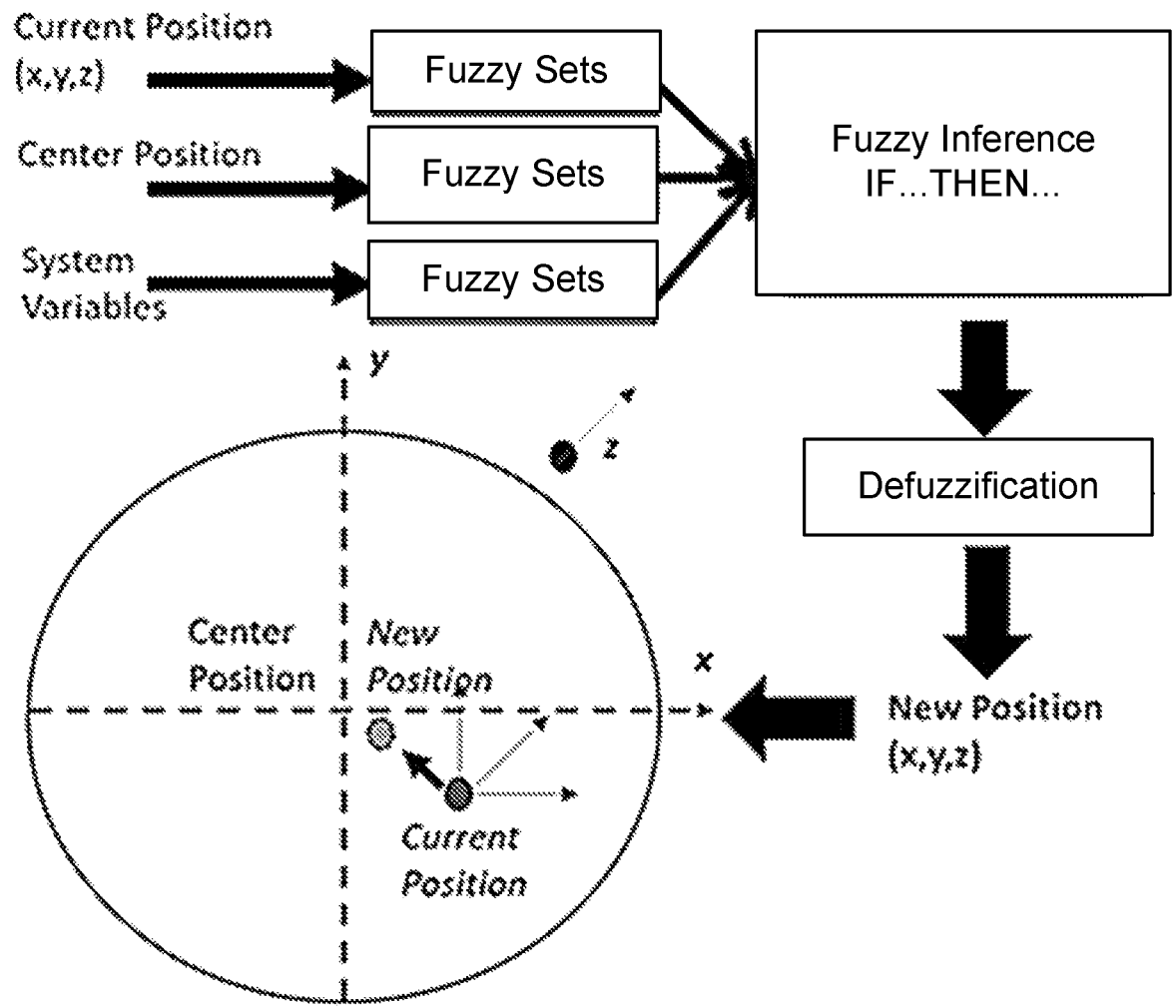
FIG. 10 shows an exemplary Artificial Intelligence (AI) navigation system schematic in accordance with various embodiments of the present disclosure.

FIG. 10 shows an exemplary AI navigation system schematic demonstrating feedback of sensor data from positional sensors and system variables to guide robot navigation in an automated manner while accounting for flow within a passageway, such as a vessel, bowel, tracheobronchial tree, etc. As discussed, an exemplary fuzzy logic navigation control can utilize fuzzy sets that model the input (current position of the robot in 3D coordinates i.e., x, y, z and the vessel boundary or bronchus bowel lumen, from computed tomography angiograph (CTA), intravascular ultrasound (IVUS), optical fiber, other sensor, etc. and output (intended destination in 3D coordinates) variables. Fuzzy rules (e.g., define how the position of the EFMR and boundaries of the passageway (vessel boundary, bronchus bowel lumen, etc.) are used to calculate an intended destination) and the defuzzification component (e.g., communicates precise control directions to the EFMR tool). Modeling via fuzzy rules allows the easy expansion of the system by incorporating more information upon availability. AI incorporation will allow the operator to switch between AI-guided navigation mode and a manual control mode for surgery interventions, in various embodiments.

Figure 11:
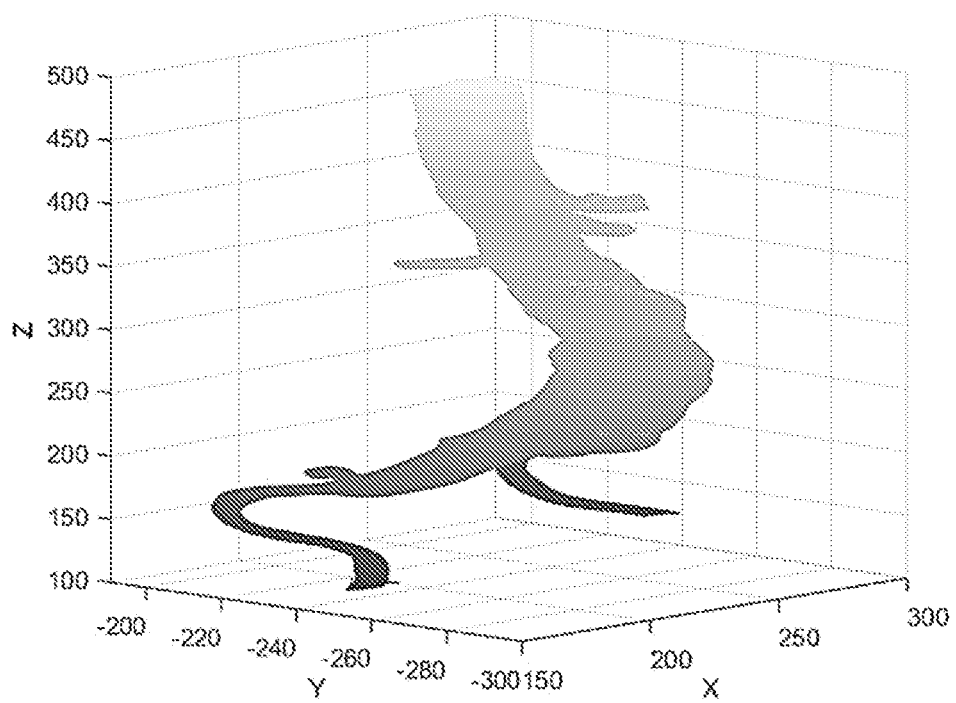
FIG. 11 shows a 3D image of an aorta used for navigation system testing of an exemplary navigation system in accordance with various embodiments of the present disclosure.

As part of an evaluation of an exemplary fuzzy navigation system, the system has been demonstrated on a real human aortic anatomy simulation, in which the aortic model is simulated from Computational Tomography data reconstructed in 3 dimensions using the Matlab software. Accordingly, FIG. 11 shows a 3D image of the testing aorta, where we observe that it has two branches in the lower part. The navigation path starts from the large right aortic branch (right iliac artery), as shown in FIG. 11, and moves upwards (towards the heart—not depicted here) until the microrobot reaches a top end of the 3D model (supraceliac aorta). In this testing, the movement in the Z axis is constant and the microrobot moves 2 mm at every time slot. The time slots can be determined by the system modeler, and their length can depend on the surgeon and the needs at each time. For testing purposes, the time slots are defined to be equal to 5 seconds.

By applying an exemplary fuzzy navigation system to the aorta in FIG. 11, we obtain the path that it will be followed by the microrobot once it is inside the aorta. In particular, the paths are presented in the two planar images—i.e., X-Z and Y-Z planes—that are provided in FIGS. 12 and 13, where the target location at the end of each time slot is given. The simulated movement within the aorta exhibits the ability of an exemplary fuzzy navigation system to make decisions over the movement of the microrobot with the goal of remaining as close as to the center of the aorta. In reality, the movement of the microrobot within the aorta will be imposed to several difficulties. Therefore, the uncertainty in its movement emerges from the following factors: (i) the information within the aorta may not be highly accurate due to imaging techniques and measurement instruments, and (ii) the varying environment across the pathway of the microrobot (for instance other smaller branches).

Figure 12:
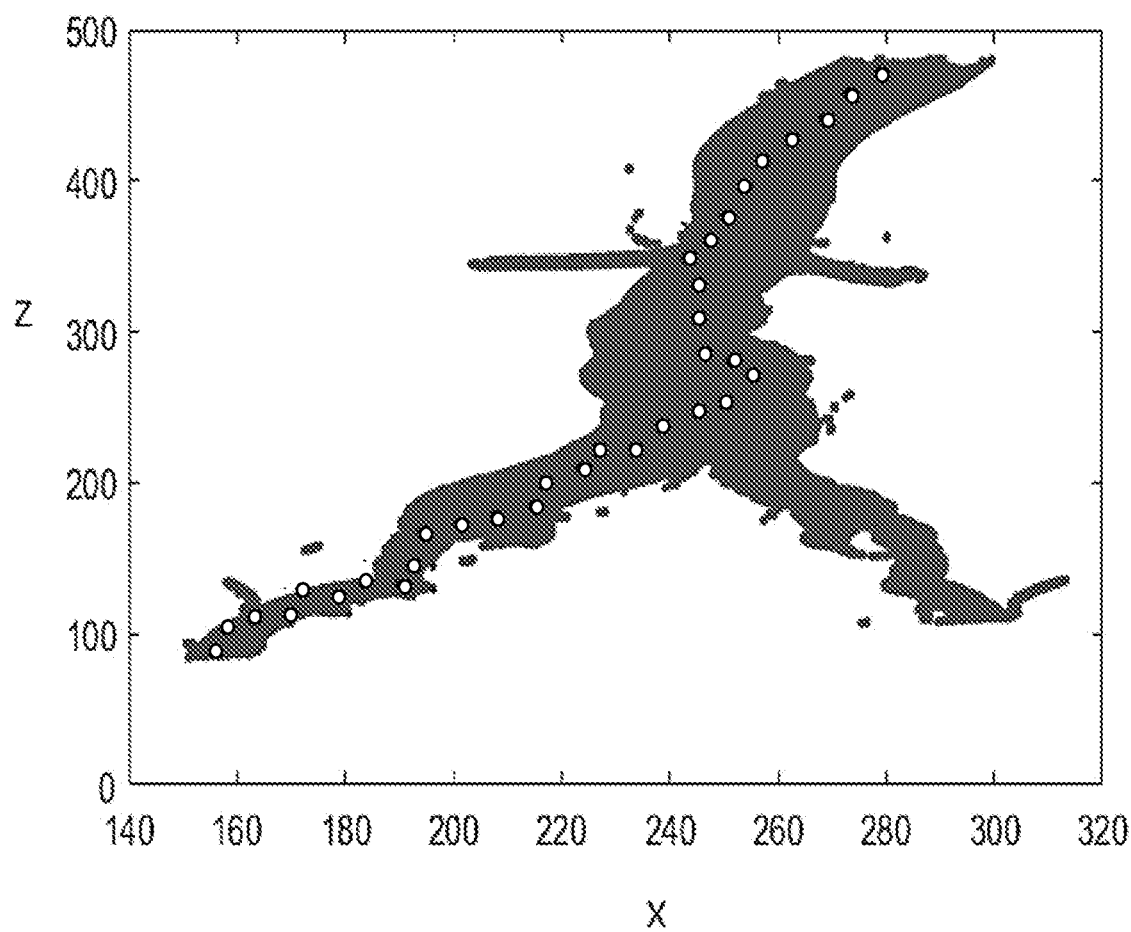
FIG. 12 shows a navigation path in the X-Z plane of the testing aorta for a microrobotic tool utilizing an exemplary navigation system in accordance with various embodiments of the present disclosure.
Figure 13:
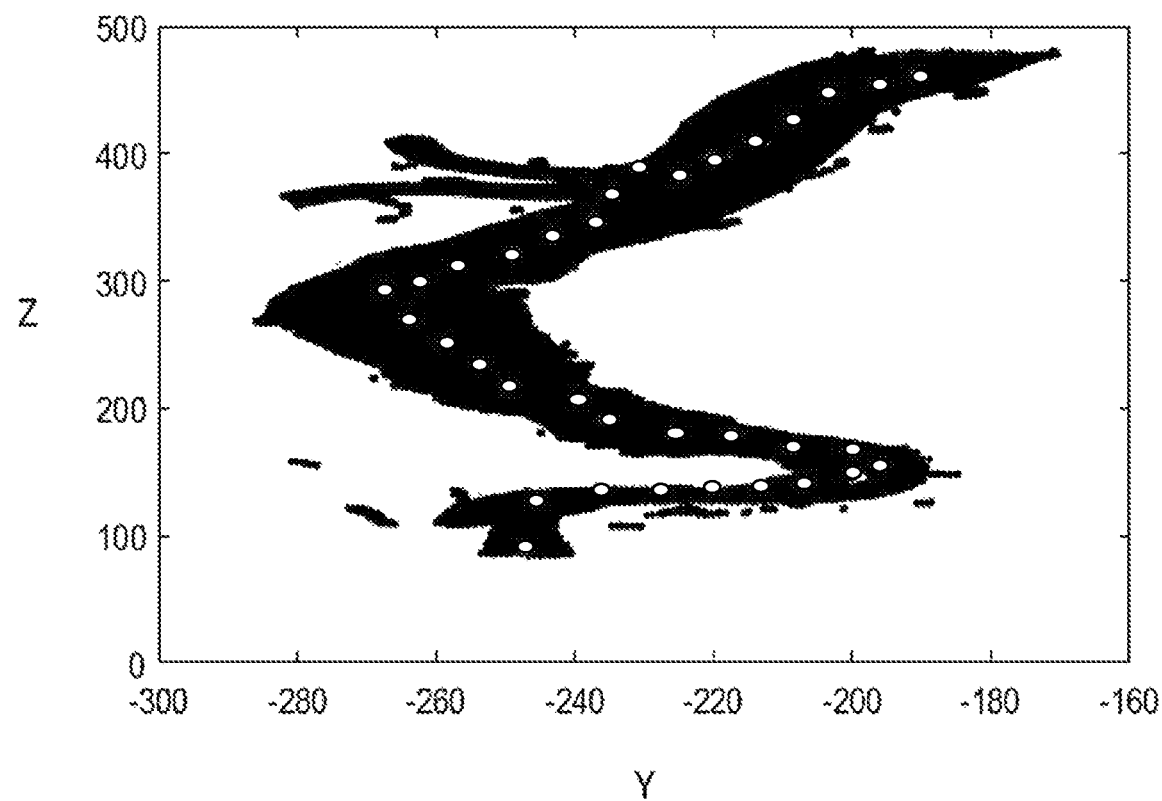
FIG. 13 shows a navigation path in the Y-Z plane of the testing aorta for a microrobotic tool utilizing an exemplary navigation system in accordance with various embodiments of the present disclosure.

In FIGS. 12 and 13, it is assumed that the motion of the robot is not impeded by the blood flow and the information is accurate. Furthermore, it is assumed that every navigation decision was made at the end of each time slot. Thus, the movement was made, the current position at the end of the time slot was recorded, and based on the current position, the next movement was decided by the fuzzy navigation system. Therefore, it is observed that the fuzzy navigation system provided the path followed across the two planar images (recall that in the Z axis the motion is constant). It can be observed that branches that connect to the main aorta cause the fuzzy navigation to move away from the center of the aorta (this is apparent in the position 350, 240 in FIG. 12). Despite this drawback, the exemplary system managed to provide a pathway that is very close to the optimal one (always at the center). This observation exhibits the strengths of fuzzy logic to handle uncertainties in the movement and make "smart" decisions over the next movement.

It can be noted that the fuzzy navigation system under test provided a short time in traversing the aorta. The overall simulation of the movement was equal to 171 seconds. The majority of time was taken by the predetermined time slots, while the decision-making process was less than 0.01 seconds at each instance. In any case, the navigation system under test is as fast as an expert vascular surgeon, for the time needed if the navigation was managed by conventional means. This fast processing is the direct result of adopting fuzzy logic tools for implementing the navigation systems.

Therefore, an exemplary navigation system does provide a fast and dynamic decision-making for autonomous navigation in aortic environments in a satisfactory way. In various embodiments, an exemplary fuzzy navigation system may have its resolution increased by adding a higher number of fuzzy sets and fuzzy rules.

An embodiment of the above-described microrobotic system is capable of multiple functionalities, which may include (1) three-dimensional expansion flexible microrobotic navigation, (2) endograft deployment guidance, (3) ancillary systems compatibility for the already utilized devices in the market (e.g., stent-grafts, wires, catheters, sheaths, laser fibers, intravascular ultrasound systems), (4) real-time imaging, (5) real-time wall stress monitoring, (6) endo-repositioning, (7) endovascular trash retrieval, (8) emergent intravascular shunting-reperfusing, (9), in situ fenestration ability, and (10) artificial intelligence integration.

The above-described embodiments for the microrobotic system provide multiple advantages over existing technologies. Such microrobotic systems have a major advantage in accessing anatomical structures with complex morphology and anatomy, conforming to the pathway without injuring the tissues, and creating a supported safe access shaft for other instruments. The EFMR motion provides the unique ability to navigate in a less traumatic fashion, which is beyond the capacity of the human hand and existing medical devices. Another advantage is that, by increasing the ability to manipulate structures with the microrobotic system, one decreases the need for larger incisions for access and reduces the discomfort associated with larger instruments.

The microrobotic system also adds further refinement of control with artificial intelligence and provides the ability to emulate surgical instruments with more flexible and three-dimensional navigation capacity so as to enable access to more distant and difficult to reach targets. The microrobotic system also provides the capability to decrease operative time, increase accuracy and control of the operation, and decrease the need for advanced operator skills.

The microrobotic system has MRI compatibility, which is a major advantage over current systems. Although existing microrobotic surgical tools have various benefits, no such system is MRI compatible. For example, an exemplary robotic shaft and its microrobotic components can be created by material without strong magnetic properties—thus the MRI magnetic field will not be able to create any effects on the portion of the robot inside a fluidic passageway, such as vessels, bowel, or tracheobronchial tree.

The microrobotic system can be used to create a stable support system for accurate endograft placement without the need for multiple ancillary devices (e.g., wires, catheters, and sheaths). This contributes to the reduction of the operative time (especially in emergency situations) as well as the cost of the procedure.

The microrobotic system also provides the ability for endo-repositioning of endografts (e.g., adjusting the location of an endograft in the aortic lumen) in occasions of graft migration and acute malperfusion (e.g., acute occlusion of critical branches of the aorta). The system also facilitates control of complications, such as aortic rupture and aortic branch reperfusion in patients having acute aortic trauma.

The microrobotic system protects the vessel wall from stress in order to prevent vessel-wall injuries during endograft deployment (e.g., stress in the aortic wall from the insertion of grafts and devices through the lumen). The microrobotic system also supports in situ mechanical retrieval of endovascular trash and laser fibers for in situ graft fenestration (i.e., the ability to place openings on the endografts allowing for redirection of the blood supply).

From a surgical-operative standpoint, except for the properties as described above, the microrobotic system decreases the operative time and, therefore, decreases the need for extensive radiation use (fluoroscopy time for current complex aortic interventions can be as high as 120 minute of continuous radiation), which can be harmful for the operator and the patient. The enhanced performance of the microrobotic system simplifies complex interventions and makes them more feasible in emergency conditions, whether they be in civilian or military settings.

The broad compatibility of the microrobotic system with various current medical devices provides an advantage for the implementation of the microrobotic system in the market as it can not only be used in concert with current medical devices but also can correct complications secondary to the failure of those devices. The microrobotic system provides an additional measure for the prevention of access vessel dissection or more sensitive carotid vessel dissection as it uses expansion and rolling for navigation in the lumen versus blunt force "pushing" and friction.

In addition, the controlled stiffness reduces the chances of rupturing of calcified tortuous access vessels (e.g., calcified iliac vessels) while simultaneously providing a stable system for interventions that requires less complexity in terms of components and required actions (e.g., soft wire and catheter, subsequent exchange for stiffer wire, subsequent insertion of a sheath past the aortic arch, further exchange for soft wire and catheter for further navigation in the extracranial carotid system, further device exchange for suction of the thrombus, etc.). Instead, a single microrobotic system with artificial intelligence support is provided for fast access within vessels (e.g., the carotid circulation for cerebrovascular interventions).

Specific applications in which the microrobotic systems can be used include the following examples. (a) Aortic and major vessel interventions for traumas, ruptures, aneurysms, dissection, acute malperfusion/ischemia. Utilized by vascular surgery, cardiac surgery, cardiology, and interventional radiology for aortic and major vessel interventions, thoracic, abdominal, paravisceral, cerebrovascular, and peripheral applications; (b) the broad compatibility of the microrobotic system with the various currently utilized commercial devices provides the advantage to correct complications secondary to the failure of these devices. Broad compatibility with the majority of the various commercialized FDA-approved endovascular stent and grafts allow concurrent use and increase the applicability of these devices; (c) acute ischemic stroke and cerebrovascular thrombectomies; and (d) endovascular debranching which was previously not possible.

For example, the microrobotic system provides the ability to introduce through a peripheral vessel, such as the femoral arteries or the brachial/axillary arteries, expansion flexible cannulation units that will navigate to the targeted aortic branches and subsequently create a direct pathway for extracorporeal perfusion to be implemented. This is assisted with artificial intelligence navigation and dynamic feedback from the vessel wall (e.g., stress, flow, and pressure). With such functionality, one can perfuse selected aortic branches in order to control blood flow in the aortic lumen for an intervention, such as repair. Currently, the only way to achieve this is through open and risky interventions, such as a debranching bypass. The microrobotic system enables shorter operative times, faster vital organ reperfusion, decrease of the operative complexity, and the possibility for better management and decreased mortality in aortic interventions, which currently have high morbidity and mortality. This will facilitate control of complications, such as aortic rupture and aortic branch reperfusion (enabling redirection of the blood supply in vital organs). Moreover, the system will obtain and deliver real-time feedback for vessel wall stress in order to prevent vessel wall injuries during the deployment (i.e., stress in the aortic wall from the insertion of devices through the lumen).

The present disclosure also introduces a novel fuzzy driven system that can support navigation operations through tubular passageways, such as endovascular operations. Such systems are able to provide the ability for accurate, autonomous, and fast navigation of a microrobot within the aorta, while decreasing the operator's effort. Implementation of an exemplary navigation system adopted tools from artificial intelligence and more specifically from fuzzy logic. In particular a FIS was designed that takes into consideration the current position of the microrobot and provides the angles at which the microrobot should move within the next time slot. The use of fuzzy logic accommodated fast decision-making process that is as fast as an expert endovascular surgeon, without compromising navigation accuracy. Furthermore, the path was decided by the FIS system with no human intervention. An exemplary navigation system was tested in a case with a real-world aortic imaging data. Testing showed that the path followed was a nearly optimal path while the navigation time was very low (171 sec).

Figure 14:
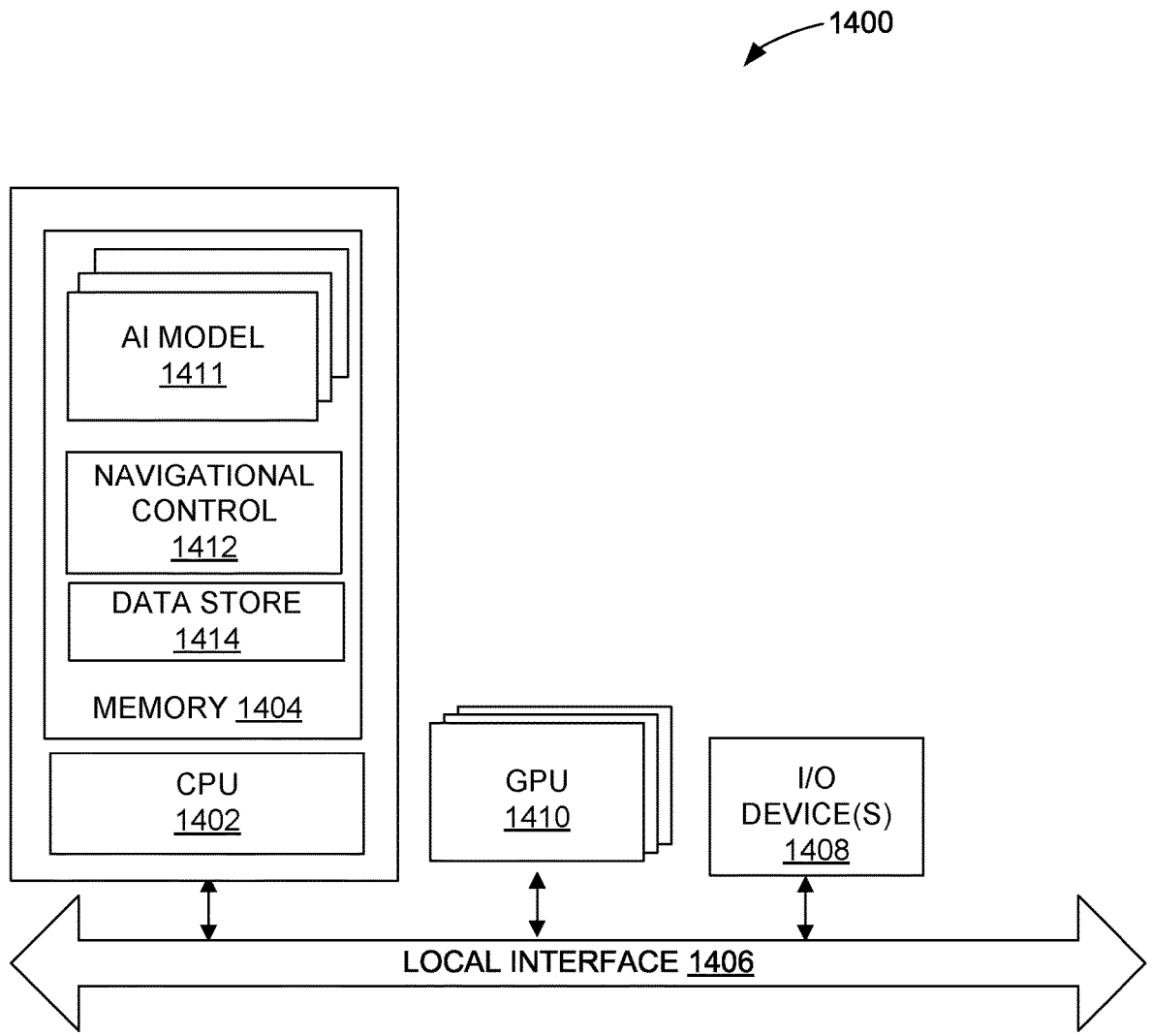
FIG. 14 depicts a schematic block diagram of a computing device that can be used to implement various embodiments of the present disclosure.

FIG. 14 depicts a schematic block diagram of a computing device 1400 that can be used to implement various embodiments of the present disclosure, such as computer 106. An exemplary computing device 1400 includes at least one processor circuit, for example, having a processor 1402 and a memory 1404, both of which are coupled to a local interface 1406, and one or more input and output (I/O) devices 1408, such as sensing devices or sensors. The local interface 1406 may comprise, for example, a data bus with an accompanying address/control bus or other bus structure as can be appreciated. The computing device 1400 further includes Graphical Processing Unit(s) (GPU) 140 that are coupled to the local interface 1406 and may utilize memory 1404 and/or may have its own dedicated memory. The CPU and/or GPU(s) can perform various operations such as fuzzy logic operations described herein.

Stored in the memory 1404 are both data and several components that are executable by the processor 1402. In particular, stored in the memory 1404 and executable by the processor 1402 are code for implementing one or more artificial intelligence models or networks 1411 (e.g., fuzzy logic models) and code 1412 for using the artificial intelligence models 1411 for navigational control of a microrobotic tool within a passageway, such as a fluidic tube, vessel, bowel, etc. Also stored in the memory 1404 may be a data store 1414 and other data. The data store 1414 can include a video feed or other sensing data from I/O devices 1408, and potentially other data. In addition, an operating system may be stored in the memory 1404 and executable by the processor 1402. The I/O devices 1408 may include input devices, for example but not limited to, a keyboard, mouse, etc. Furthermore, the I/O devices 1408 may also include output devices, for example but not limited to, a printer, display, etc.

Certain embodiments of the present disclosure can be implemented in hardware, software, firmware, or a combination thereof. If implemented in software, the navigational control logic or functionality is implemented in software or firmware that is stored in a memory and that is executed by a suitable instruction execution system. If implemented in hardware, the navigational control logic or functionality can be implemented with any or a combination of the following technologies, which are all well known in the art: discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It should be emphasized that the above-described embodiments of the present disclosure are merely possible examples of implementations, merely set forth for a clear understanding of the principles of the disclosure. Many variations and modifications may be made to the above-described embodiment(s) without departing substantially from the principles of the disclosure. All such modifications and variations are intended to be included herein within the scope of this disclosure and protected by the following claims.

The invention claimed is:

1. A robotic system comprising:
a robotic surgical tool, wherein the robotic surgical tool comprises an elongated, flexible, steerable cannula that includes multiple expansion-flexion microrobotic (EFMR) cannulation units (CUs) that are configured to be selectively stiffened or softened using non-Newtonian fluid compression;
a steering system configured to steer the robotic surgical tool based on motion angle commands along X and Y axes as the robotic surgical tool moves in an Z axis direction within a tubular passageway; and
a computing device that executes an artificial intelligence program configured to control the steering system by computing the motion angle commands based on a current position of the robotic surgical tool along X & Z planar axes and Y & Z planar axes of the tubular passageway and center positions of the tubular passageway along the X & Z planar axes and the Y & Z planar axes.

2. The system of claim 1, wherein the robotic surgical tool is configured to move via flexible microrobotic expansion.

3. The system of claim 2, wherein the artificial intelligence program utilizes a fuzzy logic model to determine the motion angle commands.

4. The system of claim 3, further comprising an imaging device that acquires real-time images of the current position of the robotic surgical tool within the tubular passageway and provides the real-time images to the computing device.

5. The system of claim 4, wherein the fuzzy logic model is configured to process the real-time images to produce fuzzy input parameters corresponding to the current position of the robotic surgical tool; processes the fuzzy input parameters to produce fuzzy output parameters corresponding to motion angles for a next move of the robotic surgical tool; and processes the fuzzy output parameters to derive motion angle values at which the robotic surgical tool is to be steered.

6. The system of claim 4, wherein the real-time images comprise computed tomography angiograph (CTA) or intravascular ultrasound (IVUS) images.

7. The system of claim 1, wherein the tubular passageway comprises an aortic lumen or a bowel lumen.

8. The system of claim 1, wherein the robotic surgical tool comprises an endograft instrument.

9. A method for steering a robotic surgical tool, the method comprising:
acquiring, by a computing device, sensor data indicating a current position of the robotic surgical tool within a tubular passageway, wherein the robotic surgical tool comprises an elongated, flexible, steerable cannula that includes multiple expansion-flexion microrobotic (EFMR) cannulation units (CUs) that are configured to be selectively stiffened or softened using non-Newtonian fluid compression;
determining, by the computing device, the current position of the robotic surgical tool along X & Z planar axes and Y & Z planar axes of the tubular passageway and center positions of the tubular passageway along the X & Z planar axes and the Y & Z planar axes;
computing, by the computing device, motion angle commands that will steer the robotic surgical tool at a constant speed forward through the tubular passageway along a Z axes; and
sending, by the computing device, the motion angle commands to a controller for the robotic surgical tool.

10. The method of claim 9, further comprising stiffening the robotic surgical tool and inserting a stiff device within a cavity of the robotic surgical tool.

11. The method of claim 10, wherein the stiff device comprises a surgical stent.

12. The method of claim 9, wherein the robotic surgical tool is configured to move via flexible microrobotic expansion.

13. The method of claim 9, wherein the computing device utilizes a fuzzy logic model to determine the motion angle commands.

14. The method of claim 13, wherein the sensor data comprises real-time images of the current position of the robotic surgical tool within the tubular passageway.

15. The method of claim 14, wherein the fuzzy logic model processes the real-time images to produce fuzzy input parameters corresponding to the current position of the robotic surgical tool; processes the fuzzy input parameters to produce fuzzy output parameters corresponding to motion angles for a next move of the robotic surgical tool; and processes the fuzzy output parameters to derive motion angle values at which the robotic surgical tool is to be steered.

16. The method of claim 14, wherein the real-time images comprise computed tomography angiograph (CTA) or intravascular ultrasound (IVUS) images.

17. The method of claim 9, wherein the tubular passageway comprises an aortic lumen or a bowel lumen.

18. The method of claim 9, wherein the robotic surgical tool comprises an endograft instrument.

* * * * *